Figure 1:
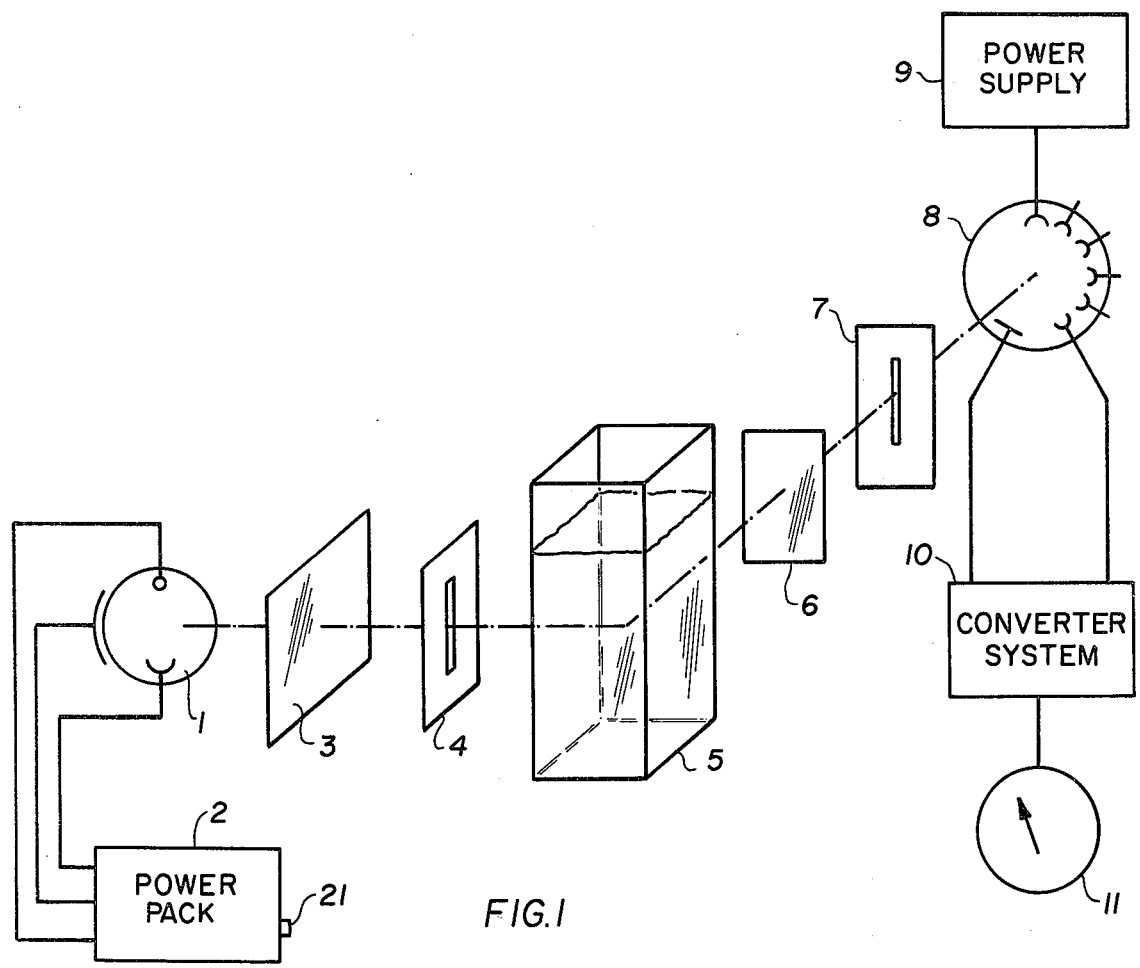

United States Patent [19]

Noller

[11] 4,133,873

[45] Jan. 9, 1979

[54] METHOD OF DETERMINING EXTRACELLULAR ANTIGENS AND ANTIBODIES

[76] Inventor: Hans G. Noller, 1512 Basswood Cir., Glenview, Ill. 60025

[21] Appl. No.: 689,335

[22] Filed: May 24, 1976

[30] Foreign Application Priority Data

May 26, 1975 [DE] Fed. Rep. of Germany ....... 2523209

[51] Int. Cl.² ..................... G01N 21/52; G01N 33/16
[52] U.S. Cl. .................................... 424/8; 23/230 B; 250/458; 424/12
[58] Field of Search ..................... 23/230 B; 424/8, 12

[56] References Cited

U.S. PATENT DOCUMENTS

| 3,646,346 | 2/1972 | Catt | 23/230 B X |
| 3,789,116 | 1/1974 | Kay | 424/8 |
| 3,901,654 | 8/1975 | Gross | 23/230 B |
| 3,935,074 | 1/1976 | Rubenstein | 23/230 B |
| 4,020,151 | 4/1977 | Bolz | 23/230 B |

OTHER PUBLICATIONS

Chemical Abstracts, 75:45466w (1971).

*Primary Examiner*—Sidney Marantz
*Attorney, Agent, or Firm*—Hans Berman

[57] ABSTRACT

Hepatitis associated antigen (HAA) in human blood serum is precipitated on HAA-specific antibodies immobilized on the inner wall of a plastic tube. A solution of HAA-specific antibodies tagged with fluorescein is held in contact with the deposited antigens until a portion of the antibodies from the solution is affixed to the antigens. The residual, tagged antibodies in the solution are exposed to a light pulse, and the resulting fluorescence is measured as an inverse indication of HAA in the blood serum.

9 Claims, 2 Drawing Figures

METHOD OF DETERMINING EXTRACELLULAR ANTIGENS AND ANTIBODIES

This invention relates to the determination of antigens and antibodies in blood, and more particularly to a method of determining the amount of extracellular antigens or antibodies.

The best method available to the clinical laboratory for determining amounts of antigens and antibodies in blood of humans and others is radio immune assay (RIA), but the method has not found acceptance in the routine testing of blood for the presence of hepatitis associated antigens although serum hepatitis after blood transfusions is a serious and sometimes fatal complication of many medical procedures.

Radio immune assay requires highly trained technicians capable of observing the precautions necessary in handling radioactive materials. The isotope-tagged reactants employed in RIA have a limited shelf life which makes their use costly. There is an urgent need for a simpler and less expensive method of determining extracellular antigens and/or antibodies in blood.

It has now been found that antigens and antibodies may be tagged with fluorescent materials, and that the amounts of the tagged antigens or antibodies can be determined by measuring the secondary light emission from the tagged antigens or antibodies when the same are exposed to brief pulses of very intense light.

The fluorescent tagging of antigens and antibodies is not new in itself. It was first described by A. H. Coons et al (Proc. Soc. Exp. Biol. & Med. 47, [1941] 200–202) and much information on the subject is found in the "Handbook of Experimental Immunology" (D. M. Weir ed., F. A. Davis Co., Philadelphia, Pa.) and in a paper on "Fluoerescent Antibody Techniques" by W.B. Cherry (U.S. Dept. of HEW, 1960).

The known methods are limited to microscopic examination of intracellular antigens and to the fluorescent tagging of antibodies to a limited extent. When the known methods are scaled up to specimens useful in the clinical laboratory, the light necessary for producing fluorescence causes irreversible damage to the antigens and antibodies as well as decomposition (bleaching) of the fluorescent materials employed for tagging. The specimens and the fluorescent material deteriorate during the exposure to exciting light at such a high rate that the readings on the intensity of the secondary light emission cannot be correlated in a meaningful manner to the amounts of antigen or antibody originally present.

It has now been found that the long irradiation periods employed heretofore are unnecessary, and that a pulse of light too short to cause significant decomposition of the fluorescent material or of the tagged biological material will excite sufficient secondary radiation for precise quantitative determination by electronic sensing methods which permit a perceptible signal to be generated.

Pulses as short as $10^{-5}$ second are sufficient in many instances and a pulse duration of $10^{-3}$ second is rarely necessary. Suitable pulses are emitted by commercially available, electronic flash tubes which release a primary light beam of adequate intensity in a short period.

Many fluorescent materials effective for tagging antigens and antibodies are known and commercially available. Fluorescein isothiocyanate is merely typical of such materials and has been found to be universally applicable. The competitive binding technique and the sandwich technique customary in RIA may be employed in the method of this invention for immobilizing an antibody on a suitable carrier such as polystyrene, polypropylene, or glass (Ling et al, J. of Immunology 109 [1972] 834).

Figure 2:
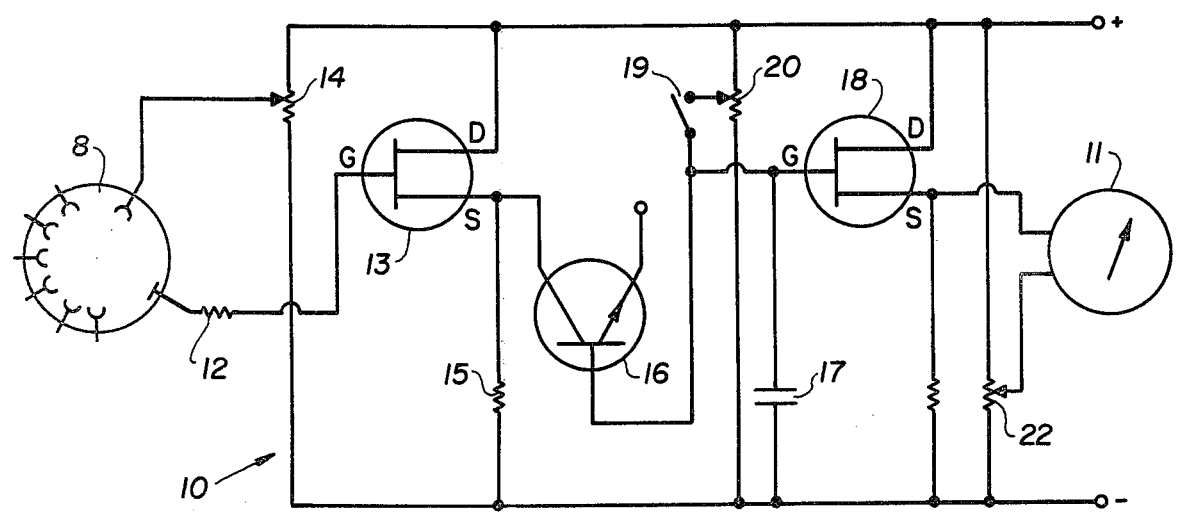

Other features, additional objects, and many of the attendant advantages of this invention will readily be appreciated as the same becomes better understood by reference to the detailed description of preferred embodiments when considered in connection with the appended drawing in which:

FIG. 1 shows apparatus for performing the method of the invention partly in simplified perspective view, and partly by conventional symbols; and FIG. 2 is a schematic of a portion of the apparatus illustrated in FIG. 1.

Referring initially to FIG. 1, there is shown an electronic flash tube 1 connected to a power pack 2 and actuated by pressing a button 21 on the pack 2 as is conventional in itself. The beam emitted by the tube 1 passes sequentially through a filter selectively permeable to a narrow spectral range at approximately 4800 Angstrom units and a collimator 4 before impinging on the tested liquid in a transparent cell 5.

Fluorescence of the tested material is caused by the exciting beam, and a portion of the fluorescent light emitted in a direction perpendicular to the incident beam is passed through another filter 6 permeable to a substantial portion of the fluorescent light at 5400 Angstrom units but opaque to light of the wavelength passed by the filter 3. After passing through another collimator 7, the filtered fluroscent light impinges on a photomultiplier tube 8 energized by a power supply 9. The output signal of the tube 8 is fed to an electronic impedance converter and memory system 10, and a voltmeter 11 connected to the system 10 indicates the intensity of the fluorescent beam received from the cell 5 by the tube 8.

As is shown in more detail in FIG. 2, the anode of the photomultiplier tube 8 is connected through a resistor 12 to the gate G of a first field effect transistor (FET) 13 operating in the source-follower mode. One of the dynodes in the tube 8 is connected to the movable contact of a voltage divider 14 whose two fixed contacts are connected to the output terminals of a source of direct current.

The secondary pulse signal generated by the FET 13 across a resistor 15 connecting the source S of the FET to the negative terminal of the current source is fed to a capacitor 17 through the collector-base junction of an n-p-n transistor 16. The transistor functions as a diode rectifier blocking current flow in a direction from the capacitor 17.

The capacitor 17 is also connected between the gate G and source S of a second field effect transistor 18 and retains its charge indefinitely unless discharged by the closing of a switch 19 connected to the movable contact of a voltage divider 20 whose fixed contacts are connected to the terminals of the current source. The voltage meter 11 is arranged in circuit between the source S of the second FET 18 and the movable contact of a voltage divider 22 analogous to the dividers 14, 20, and indicates a potential corresponding to that stored in the capacitor 17.

The following Example illustrates the method of the invention as performed with the apparatus described with reference to the drawing.

EXAMPLE

Capillary polypropylene tubes internally coated with immobilized rabbit antibodies specific for antigens associated with hepatitis B were obtained from a commercial supplier.

They were employed for checking the results of tests for hepatitis associated antigens (HAA) performed by the radio immuno assay (RIA) method on 20 specimens of human serum. Specimens Nos. 1 to 10 had been found unequivocally free of HAA by the RIA method while specimens 11 to 20 had been found by the known method to contain marginally detectable amounts of HAA.

In testing each serum specimen according to this invention, one of the polypropylene tubes was charged with 0.1 ml serum to be tested, plugged, and incubated four hours at 37° C. It was then emptied and rinsed twice with 5 ml batches of a buffer solution prepared from 0.72 g TRIS, 5.0 g NaCl, and water to make 600 ml, and adjusted to pH 7.4 with n/10 HCl.

An HAA antibody solution was prepared from the $\tau$-globulin fraction of a guinea pig serum having a high titer of HAA antibodies. The antibodies were coupled with fluorescein isothiocyanate, isomer 1, according to the method of Nairn (R. C. Nairn, "Fluorescent Protein Tracing", 3rd ed., 1969, published by Livingstone, Edinburgh & London), and diluted with 10,000 volumes of the above buffer solution.

The rinsed tube was charged with 0.1 ml of the fluorescein-tagged antibody solution, plugged, and incubated at 37° C. for 90 minutes. The contents of the tube then were diluted with 3 ml buffer solution, and the liquid mixture was exposed in the cell 5 of the apparatus illustrated in FIG. 1 to a single light flash having a duration of approximately $10^{-4}$ second.

The twenty readings respectively obtained on the serum samples were as follows:

| Sample No. | 1 | 2 | 3 | 4 | 5 | 6 | 7 | 8 | 9 | 10 |
|---|---|---|---|---|---|---|---|---|---|---|
| Volts | 7.7 | 7.9 | 7.95 | 7.2 | 3.4 | 6.65 | 7.3 | 3.15 | 7.9 | 7.2 |
| Sample No. | 11 | 12 | 13 | 14 | 15 | 16 | 17 | 18 | 19 | 20 |
| Volts | 2.73 | 2.92 | 1.94 | 1.87 | 2.83 | 1.98 | 2.81 | 2.84 | 2.7 | 2.52 |

Eight of the ten serum specimens having been found free from HAA by the RIA method gave readings of 6.65 to 7.95 V, and all specimens that had been found contaminated in the RIA test gave readings of 1.87 to 2.92 V. Samples of specimens Nos. 5 and 8 were repeatedly rechecked and gave readings closely similar to those indicated above so that specimens 5 and 8 must be assumed to contain HAA not capable of being detected by the RIA method.

In the preferred procedure outlined above, the residual antibodies in the tagged solution were determined by their fluorescence, and a low voltage reading thus indicated bonding of antibodies to the immobilized antigen on the polypropylene walls of the tubes. Precisely corresponding, inverted voltage readings were obtained in a modified procedure, in which the residual solution was discarded from each tube after incubation, and the fluorescein-tagged sandwich of antigen between two layers of antibodies was released from the tube with 0.1 N sodium hydroxide solution. The solution was neutralized with 0.1 N hydrochloric acid and tested for fluorescence in the manner described above. The modified method is more complex than that described in more detail and thus provides more opportunities for error without compensating advantages. However, the precise correlation of the readings obtained by the two methods indicates the reliability of the results listed above.

Closely analogous readings were achieved in an even more complex procedure by slitting the plastic tubes after discarding the residual antibody solution, and immersing the tube fragments in buffer solution in the cell 5 in such a manner that the primary light pulse impinged on the coated, inner tube surfaces at an angle of about 45°. Meaningful readings could also be obtained when the tube fragments were exposed dry to the light pulse.

It is also possible to tag the antigens in the serum to be analyzed with dissolved fluorescent material and to precipitate the tagged antigens on unmarked antibodies in plastic tubes as outlined above. The reduction in the secondary light emission of the residual fluorescent material in the liquid phase can be determined, but the sensitivity of this method is inherently low. Practically useful readings are obtained when the excess of fluorescent material is rinsed from the plastic tubes, and the tagged, immobilized antigens are released from the plastic wall by means of dilute sodium hydroxide solution as described above. The neutralized solution is then tested in the apparatus shown in FIG. 1.

The method of this invention has its most useful application at this time in the testing of blood for hepatitis B antigen before processing by blood banks. The preferred method, as described above, requires relatively simple and inexpensive apparatus, is capable of being carried out by semi-skilled laboratory technicians employing stable materials which are commercially available, and quickly yields reliable results. However, amounts of extracellular antigens and antibodies not associated with hepatitis can be determined by the method described above in an obvious manner.

While an inexpensive voltmeter 11 has been used successfully for displaying data commensurate with the amounts of antigens in serum, other devices may be used for generating a perceptible signal in response to the secondary light emission sensed by the photomultiplier tube 8, and other modifications of the photometer arrangement shown in FIG. 2 will readily suggest themselves to those skilled in the art.

It should be understood, therefore, that the foregoing disclosure relates only to preferred embodiments of this invention and that it is intended to cover all changes and variations of the examples of the invention herein chosen for the purpose of the disclosure which do not constitute departures from the spirit and scope of the invention set forth in the appended claims.

What is claimed is:

1. A method of determining the amount of a member of the group consisting of an extracellular antigen and an extracellular antibody capable of specifically combining with said antigen, which comprises:
    (a) tagging said member with a fluorescent material;
    (b) exposing the tagged member to a pulse of light of a first wavelength,
        (1) the intensity and duration of said pulse being sufficient to cause the emission of secondary light by the tagged exposed member without causing significant decomposition of said material, (2) said secondary light having a second wavelength different from said first wavelength;

(c) sensing said secondary light; and (d) generating a perceptible signal in response to and commensurate with the sensed secondary light.

2. A method as set forth in claim 1, wherein said duration is $10^{-3}$ to $10^{-5}$ second.

3. A method as set forth in claim 2, wherein said tagged member is present as a solute in an aqueous medium while being exposed to said pulse.

4. A method as set forth in claim 3, wherein said tagged member is in the solid state and supported on a solid carrier while being exposed to said pulse.

5. A method as set forth in claim 4, wherein said carrier and the tagged member supported thereon are immersed in a liquid during said exposing.

6. A method as set forth in claim 2, wherein said member is an antibody.

7. A method as set forth in claim 6, wherein an aqueous solution of said tagged antibody is contacted prior to said exposing with said antigen while said antigen is immobilized on a solid carrier, the amount of said tagged antibody in said solution being sufficient to permit combining of a first portion of said antibody with said antigen, whereby said portion is immobilized on said carrier, while a second portion of said antibody remains in said solution, one of said portions being exposed to said pulse.

8. A method as set forth in claim 7, wherein the exposed portion is said second portion.

9. A method as set forth in claim 7, wherein said antigen is hepatitis associated antigen.

* * * * *